(12) United States Patent
Settu et al.

(10) Patent No.: US 9,302,022 B2
(45) Date of Patent: Apr. 5, 2016

(54) SYSTEM FOR PURIFYING AIR HAVING A CATALYST FILTER

(71) Applicant: Lennox Industries Inc., Richardson, TX (US)

(72) Inventors: Vinoth Kumar Settu, Arcot (IN); Chera Selvan Neelagantan, Columbus, GA (US); Arunkumar Elango, Chennai (IN)

(73) Assignee: Lennox Industries Inc., Richardson, TX (US)

( * ) Notice: Subject to any disclaimer, the term of this patent is extended or adjusted under 35 U.S.C. 154(b) by 184 days.

(21) Appl. No.: 14/042,666

(22) Filed: Sep. 30, 2013

(65) Prior Publication Data
US 2015/0093293 A1 Apr. 2, 2015

(51) Int. Cl.
*A62B 7/08* (2006.01)
*A61L 9/00* (2006.01)
*B01D 39/20* (2006.01)
*B01D 53/88* (2006.01)

(52) U.S. Cl.
CPC .............. *A61L 9/00* (2013.01); *B01D 39/2055* (2013.01); *B01D 53/885* (2013.01); *B01D 2255/20707* (2013.01); *B01D 2255/802* (2013.01); *B01D 2257/90* (2013.01); *B01D 2259/804* (2013.01)

(58) Field of Classification Search
CPC ........................................................ A61L 9/00
USPC ................................................... 422/121, 122
See application file for complete search history.

(56) References Cited

U.S. PATENT DOCUMENTS

| 6,063,343 A * | 5/2000 | Say et al. ................... 422/186.3 |
| 2004/0170537 A1* | 9/2004 | Hara ............................. 422/122 |
| 2010/0011959 A1* | 1/2010 | Marra ............................... 96/16 |

* cited by examiner

*Primary Examiner* — Kevin Joyner
(74) *Attorney, Agent, or Firm* — Lennox Industries Inc.; Betty E. Ungerman; Osman Siddiq

(57) ABSTRACT

The present invention provides for a filter system having a catalyst filter configured for placement in a filter housing. The catalyst filter has a first band and a second band of material. Each band has a length of material extending in a longitudinal direction. Each band has a first wall and a second wall, each wall facing in an opposite direction from the other wall. A portion of each first wall is coated with a catalyst material, which receives light emitted by a light source to break down contaminants passing in air through the housing and over the catalyst material. Each of the first and second bands extends continuously along its longitudinal axis traversing the catalyst filter without being intersected by other structure of the catalyst filter. The first and second bands of material diverge relative to each other across the catalyst filter. The first wall of each band is optically exposed to light from the light source. Such light from a light source at least partially disposed to emit light between the first and second bands of material is received on the catalyst material of the first walls of both the first and second bands of material without being at least partially blocked by one of the first and second bands or other structure of the catalyst filter.

10 Claims, 12 Drawing Sheets

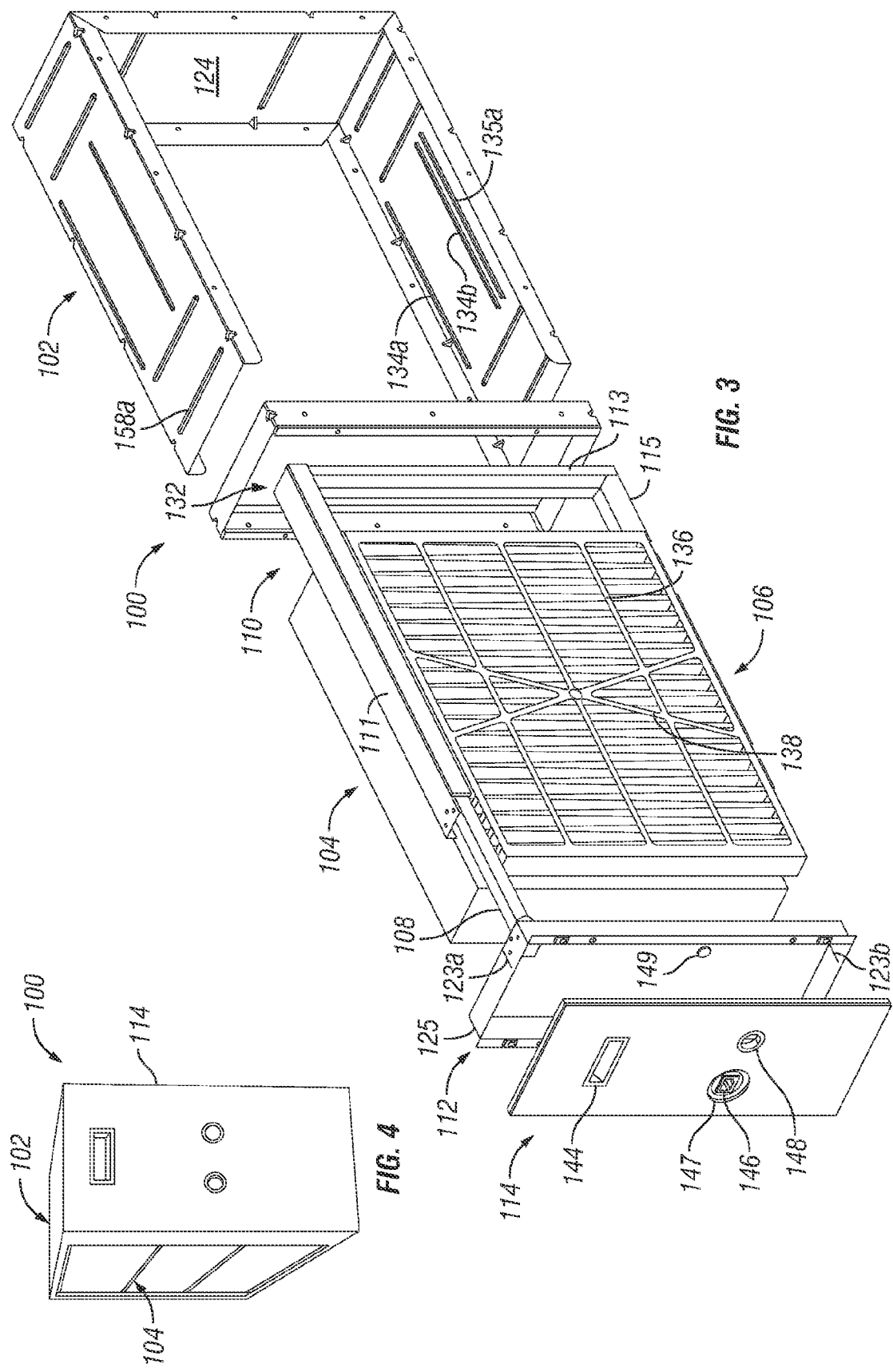

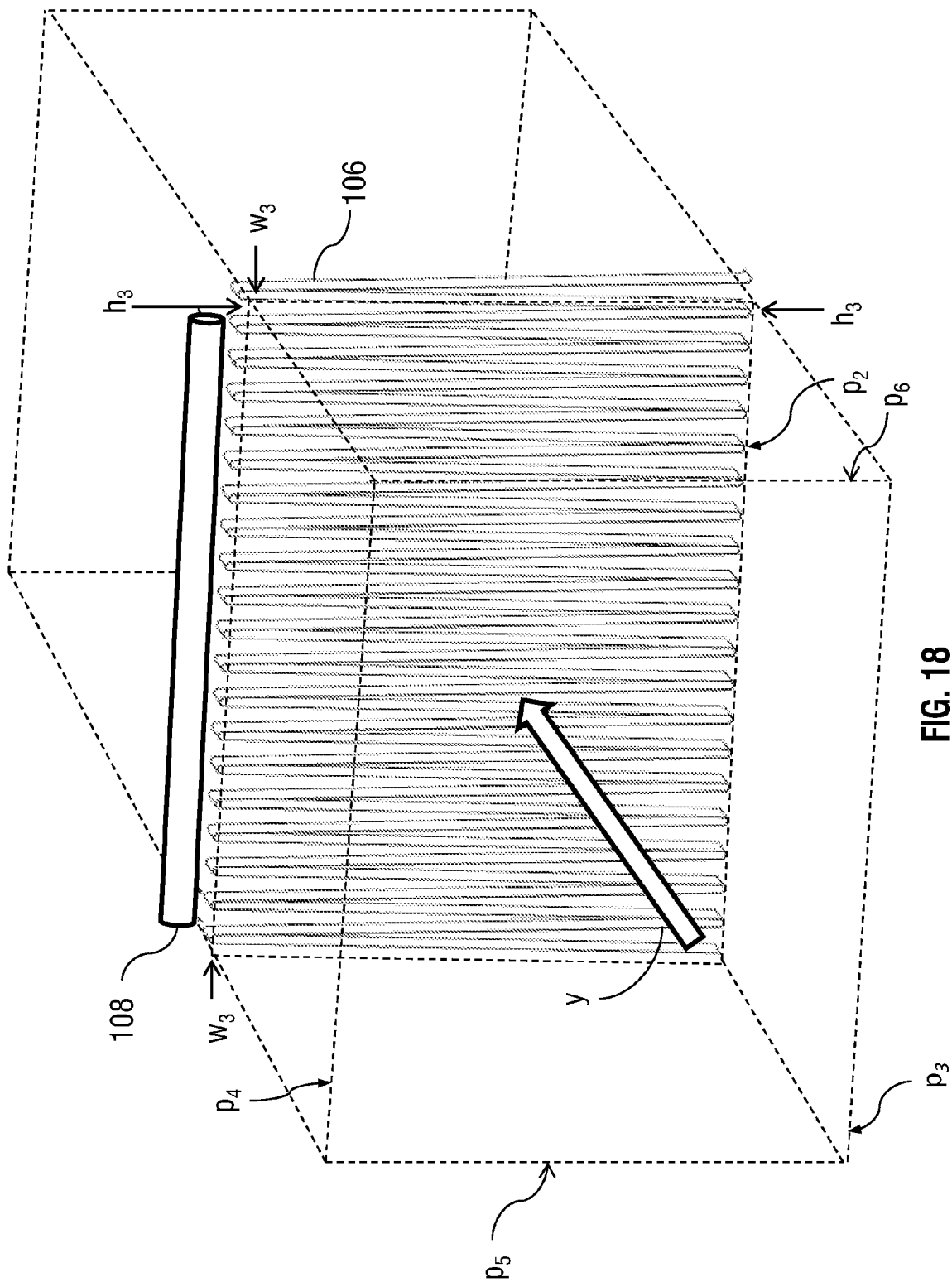

SYSTEM FOR PURIFYING AIR HAVING A CATALYST FILTER

BACKGROUND

1. Field of the Invention

The present invention relates to systems for the filtration of air and, more particularly, to air filters utilizing photocatalytic oxidation.

2. Description of Related Art

Some air purification systems utilize a photocatalytic oxidation (PCO) process. The PCO process uses ultraviolet light (UV) and airborne water vapor to activate a catalyst, typically titanium dioxide. The activated catalyst generates hydroxyl radicals. The hydroxyl radicals break down contaminants in the air, such as odors, chemicals, and other organic compounds into less harmful substances, such as carbon dioxide and water.

Referring to FIG. 1, a typical and known air purification system 10 includes a pleated media filter 12, a honeycomb filter 14, and two UV lamps 16, 17 each having a reflector 18, 19, respectively. The system 10 comprises a cabin enclosure that maintains the system 10 as a single unit.

Referring to FIG. 2A, the filter 14 of the known system 10 comprises a honeycomb pattern with cells arranged in a matrix formation and contained and supported by a cardboard frame 11. The honeycomb filter 14 comprises regions of cells. In regions $T_1$ and $T_2$, the inner walls of each cell are coated with a catalyst, such as titanium dioxide. In region C, the inner walls of each cell are coated with carbon.

Referring to FIGS. 2B and 2C, each cell $T_{cell}$ of regions $T_1$ and $T_2$ has a coating 21 that covers substantially the inner walls of each cell. The walls of each cell are faced perpendicular to the direction of light coming from the lamps 16, 17, which is the same direction as the direction y of air flow through the honeycomb filter 14. The regions $T_1$ and $T_2$ cover an area of the honeycomb pattern configured to receive light from lamps 16, 17 within each catalyst coated cell.

Referring to FIG. 1, air flows from a first side $s_1$ to a second side $s_2$ through the system in a direction y. Air first is forced through to flow through the pleated media filter 12. The media filter 12 captures particles and bioaerosols. The air then passes through the honeycomb pattern of the honeycomb filter 14 where airborne water vapor and UV lamp that impacts catalyst-coated surfaces generate the hydroxyls to destroy organic compounds. The reflector is utilized to reflect light away from the media filter 12, which may degrade under prolonged exposure to UV light. Carbon-coated surfaces of the honeycomb filter further absorb the byproduct produced by the catalyst material, when the material gets activated by UV rays.

In the known system of FIGS. 1 and 2A-C, the lamps 16, 17 and reflectors 18, 19 are positioned within the airflow, along the direction y, which blocks air flow causing a drop in air pressure. The thickness $t_1$ of the lamps 16, 17 and reflectors 18, 19 also add to the width of the cabin enclosure necessary to contain the internal parts of the system 10. Accordingly, improved systems and configurations are needed to make the air purification process more efficient and cost effective, among other needs.

SUMMARY

The present invention provides for a filter system having a catalyst filter configured for placement in a filter housing. The catalyst filter comprises at least one band extending continuously in a longitudinal direction without being intersected by other structure of the catalyst filter. At least a portion of a wall of at least one band is coated with a catalyst material for breaking down contaminants in air passing through the housing and over the catalyst material. Light from a light source is received on the wall of the band without being at least partially blocked by one of the one or more bands or other structure of the catalyst filter.

BRIEF DESCRIPTION OF THE DRAWINGS

For a more complete understanding of the present invention and the advantages thereof, reference is now made to the following Detailed Description taken in conjunction with the accompanying drawings, in which:

FIGS. 3 and 4 are an assembled and an exploded view of a first filter system, respectively;

FIG. 18 is a perspective view of a catalyst filter.

DETAILED DESCRIPTION

Figure 1:
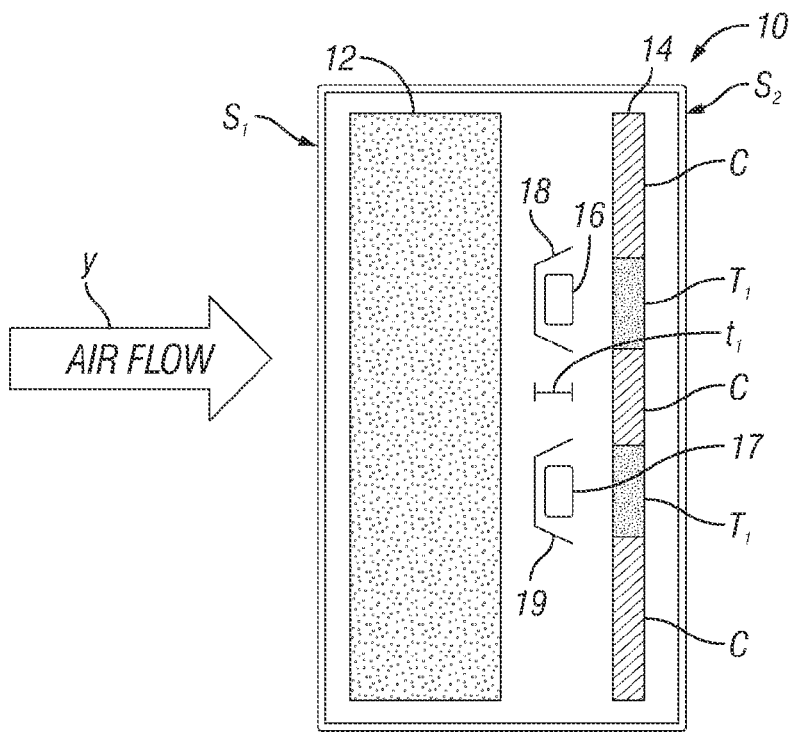
FIG. 1 is a view of a known prior art filter system.
Figure 2A:
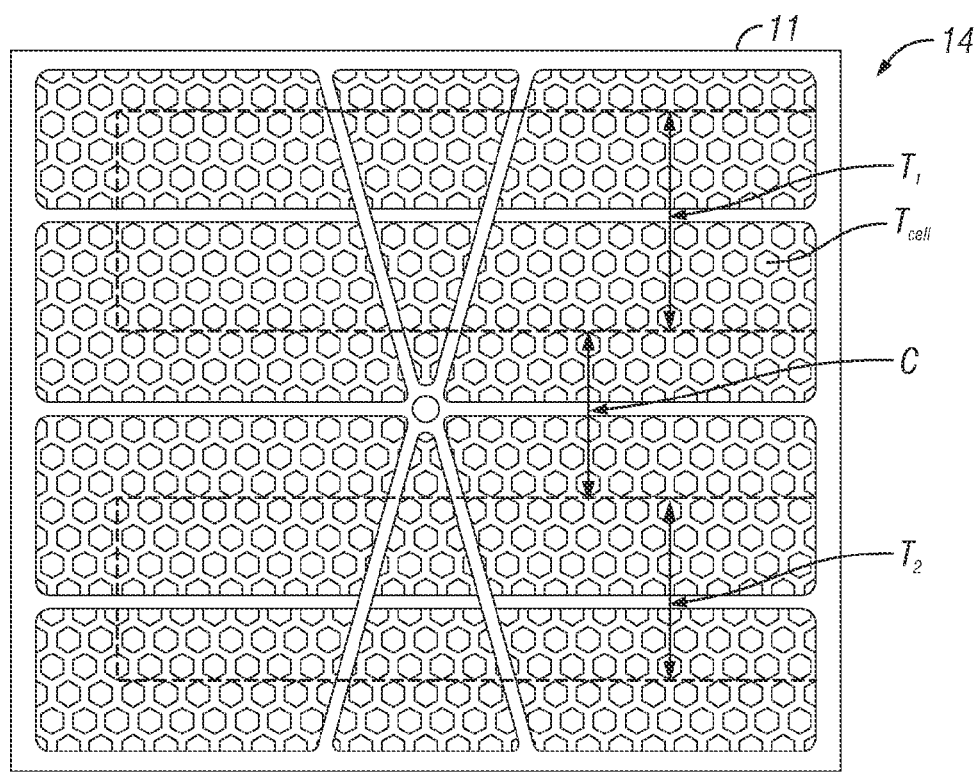
FIG. 2A is a view of a known prior art filter having a honeycomb pattern.
Figures 2B, 2C:
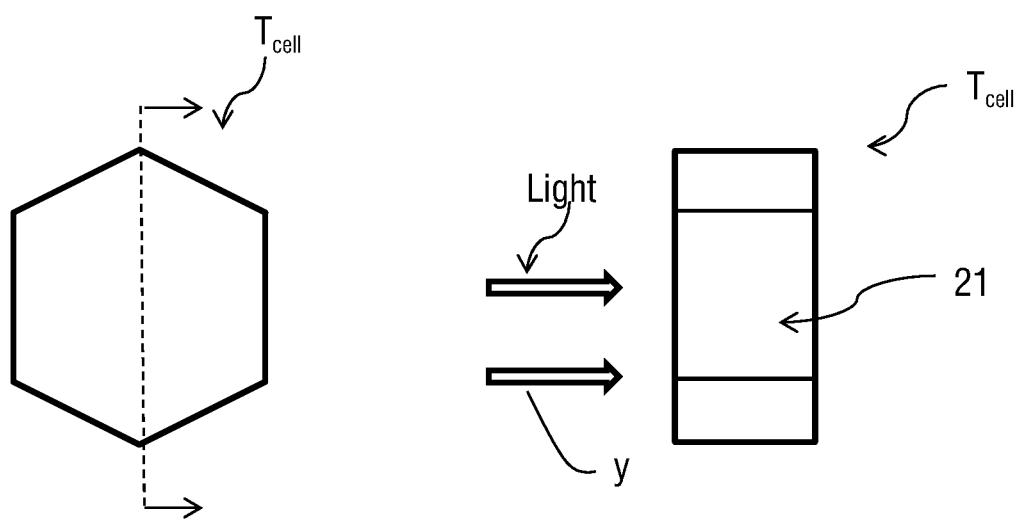
FIGS. 2B and 2C are a front view and an illustration of a cross-sectioned view of a cell of a prior art filter having a honeycomb pattern.

In the following discussion, numerous specific details are set forth to provide a thorough understanding of the present invention. However, those skilled in the art will appreciate that the present invention may be practiced without such specific details. In other instances, well-known elements have been illustrated in schematic or block diagram form in order not to obscure the present invention in unnecessary detail. Additionally, for the most part, details concerning well-known features and elements have been omitted inasmuch as such details are not considered necessary to obtain a complete understanding of the present invention, and are considered to be within the understanding of persons of ordinary skill in the relevant art.

Filter System 100

Referring to FIGS. 3 and 4, a filter system 100 may comprise a cabin enclosure 102 configured to house a filter 104, a catalyst filter 106, a light source, such as a lamp 108, a reflector 110, a control assembly 112, and a cabin door 114.

The filter system 100 is configured to filter and purify air passing first through the filter 104 and then through the catalyst filter 106.

Figure 5:
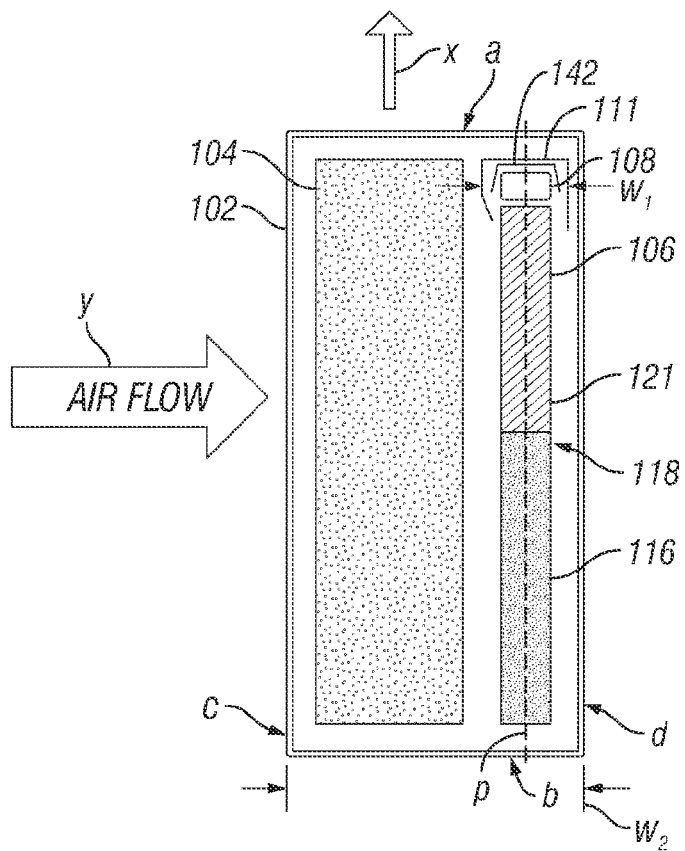
FIG. 5 is side illustration of a cross sectional view of a first filter system, showing the flow of air through a first filter system.
Figure 6:
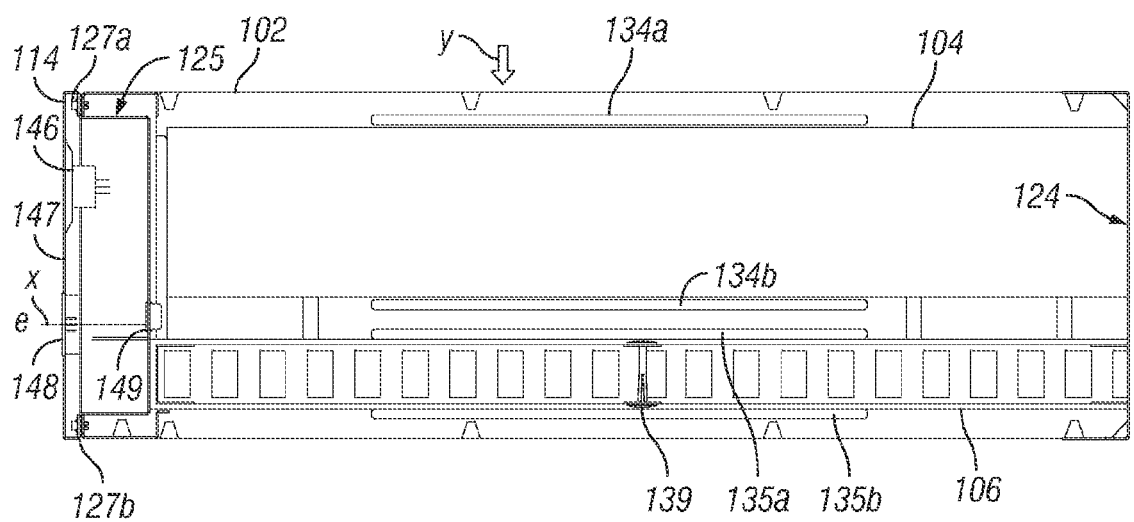
FIG. 6 is a top view of a filter system with components removed, including but not limited to a top wall and lamp, for illustration purposes.

Referring to FIGS. 5 and 6, the filter 104 and catalyst filter 106 may be aligned parallel to each other within the cabin enclosure 102 to extend in the direction x and to allow unfiltered air to pass into the filter system 100 in the direction y. For purposes of convention, first side a of the filter system 100, and its parts, will be referred to as the "top" and second side b of the filter system 100 will be referred to as the "bottom." However, it will be understood by persons of ordinary skill in the art that the filter system 100 may be used in any orientation, e.g. a vertical, horizontal, or other. Also, for purposes of convention, the side of the filter system 100, including the filter 104 and the catalyst filter 106, receiving unfiltered air will be referred to as back side c or the "back," and the side of the filter system 100 from which filtered air exits will be referred to front side d or the "front."

Figures 7, 8:
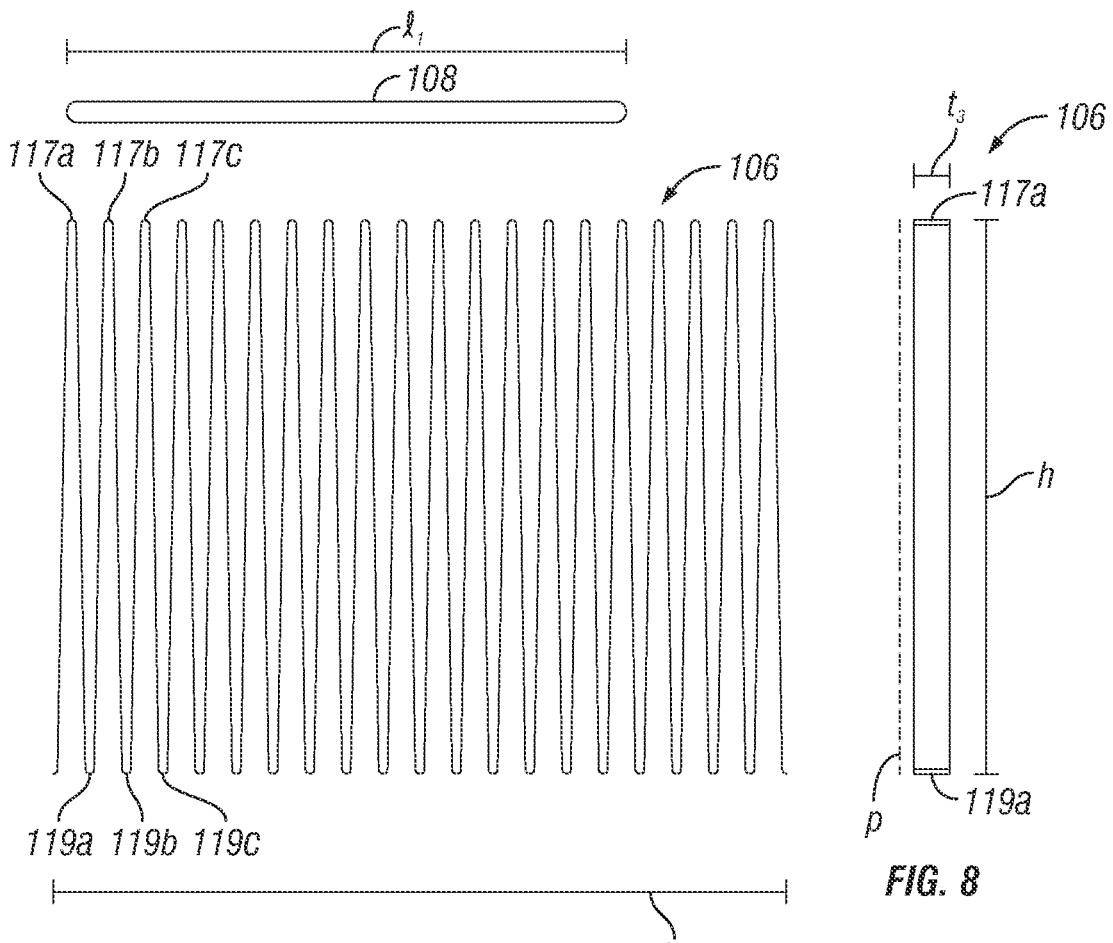
FIGS. 7, 8, and 9 are a front, side, and perspective view, respectively, of a first catalyst filter.
Figure 9:
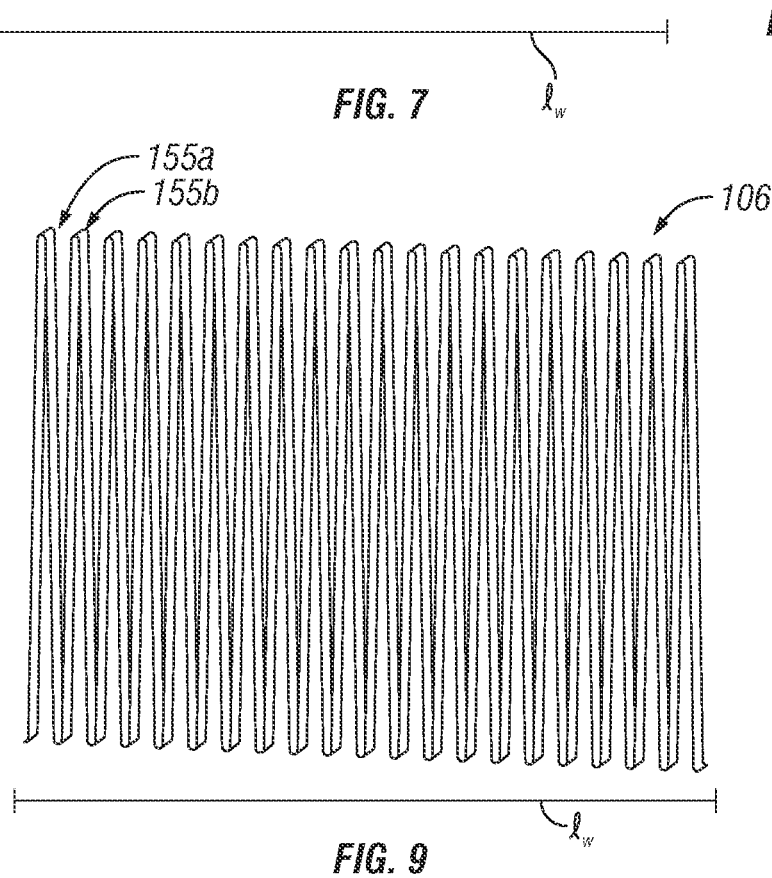

Referring to FIGS. 7, 8, and 9, the catalyst filter 106 may comprise a structure forming a filter shape. In the embodiment shown, the filter shape of the catalyst-coated surfaces will be referred to as a "wavy" pattern extending along a length $l_w$. For purposes of convention, the peaks of the wavy pattern proximal to the top side of the cabin enclosure 102 will be referred to as "crests" 117*a-c* and the valleys of the wavy pattern proximal to the bottom side of the cabin enclosure 102 will be referred to as "troughs" 119*a-c*. For convenience, only the first three crests and troughs starting from the left side of the catalyst filter are given a reference numeral. However, it will be understood by persons of ordinary that the remaining crests and troughs extending along the length $l_w$, of the catalyst filter 106 may have a similar shape, construction, and function.

Referring to FIG. 5, the wavy pattern of the catalyst filter 106 may extend substantially in a first plane p. The first plane p may face in substantially the direction y of the flow of air through the cabin enclosure 102.

Figure 10:
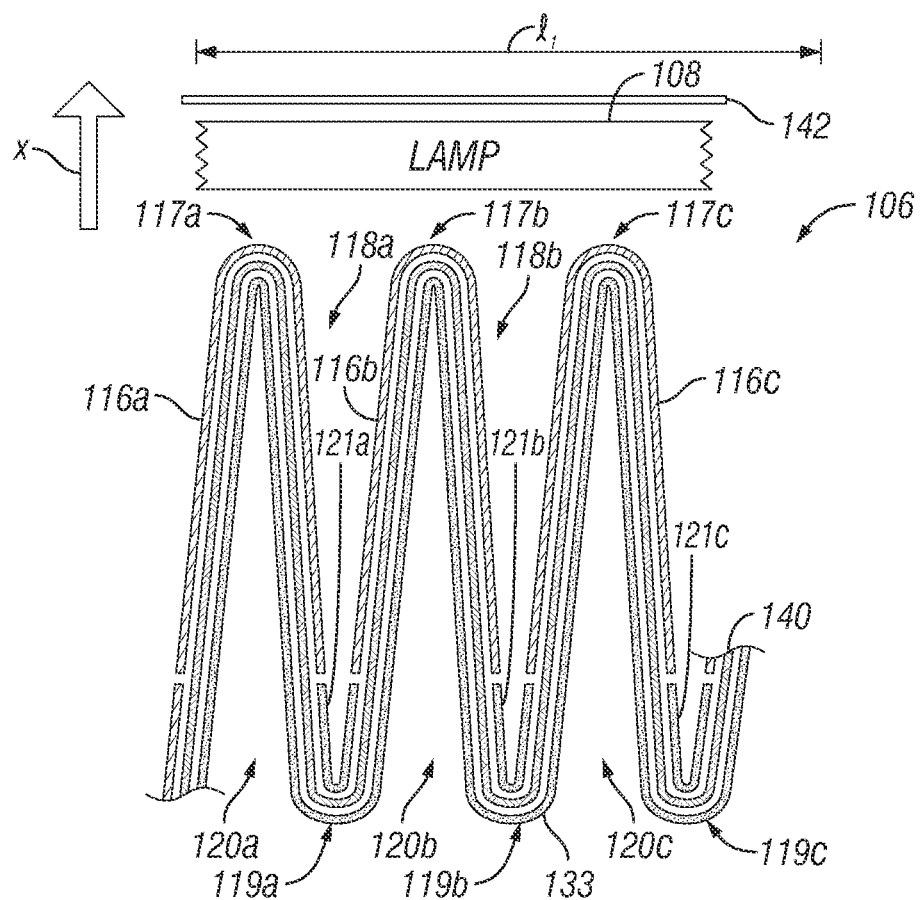
FIG. 10 is an illustration of coating on a first catalyst filter.

Referring to FIG. 10, the wavy pattern structure may comprise catalyst-coated surfaces 116*a-c* for air purification. A coating of each catalyst coated surface 116*a-c* may be applied over an underlying base structure 140.

The crests 117*a-c* and troughs 119*a-c* form top-facing corridors 118*a*, *b* and bottom facing corridors 120*a-c*, respectively. Each of the top-facing corridors 118*a*, *b* and 120*a-c* may comprise one or more of the catalyst-coated surfaces 116*a*, 116*b*, and 116*c* extending along at least a portion of the walls of the underlying base structure 140 of the catalyst filter 106. The catalyst material may comprise titanium dioxide.

Referring to FIG. 10, the wavy pattern structure may further comprise first carbon-coated surfaces 121*a-c*, which are coated with a carbon-based material for absorbing contaminants. The first carbon-coated surfaces 121*a-c* may comprise one or more carbon-coated surfaces extending along at a portion of the walls of each top facing corridor 118*a-c*, including over the crests 117*a-c*.

Referring to FIG. 10, each top-facing corridor 118*a*, *b* may comprise at least one catalyst-coated surface 116*a*, *b* and at least one first carbon-coated surface 121*a*, *b*. In some embodiments, as shown in FIG. 10, the catalyst-coated surfaces 116*a-c* are configured to extend along portions of the base structure 140 that are proximal to the lamp 108, and the first carbon-coated surfaces 121*a-c* are configured to extend along portions of the base structure 140 that are distal to the lamp 108. Positioning the catalyst-coated surfaces 116*a-c* and first carbon-coated surfaces 121*a-c* in this manner allows the catalyst-coated surfaces 116*a-c* to receive the direct light from the lamp 108 and increases the efficiency of the air purification process.

The bottom-facing corridors 120*a-c* may comprise one or more second carbon-coated surfaces 133. The second carbon-coated surfaces 133 may comprise one continuous surface extending on the base structure 140 along the bottom-facing corridors 120*a-c*, including over the troughs 119*a-c*.

The lamp 108 may be disposed to emit light onto the catalyst filter 106. Referring to FIGS. 5 and 10, the lamp 108 may be mounted proximal to the top side a of the cabin enclosure 102 within the cabin enclosure 102 so that at least a portion of the one or more of the first catalyst-coated surfaces 116*a-c* substantially faces the lamp 108 to receive direct UV light from the lamp 108. For example, the surfaces of crests 117*a-c* substantially face the lamp 108.

In the embodiments shown, at least a portion of the lamp 108 may be positioned within the first plane p to emit light substantially in the first direction into one or more of the top-facing corridors 118*a*, *b*. The lamp 108 may be positioned above the wavy structure of the catalyst filter 106 to emit along the direction x and into the top-facing corridors 118*a-c*. The one or more catalyst-coated surfaces 116*a-c* of each top-facing corridor 118*a-c* are configured to receive UV light for the purification of air.

Referring to FIGS. 3, 5, and 10, a top arm portion 111 of reflector frame 110 may be mounted above the lamp 108. The top arm 111 may comprise a reflective surface 142 configured to reflect light emitted by the lamp 108 into the top-facing corridors 118*a-c*. The reflective surface 142 may be positioned above the lamp 108 and may face toward the catalyst filter 106.

The terms "top-facing" and "bottom facing" are used for convenience to refer to the direction the corridors of the catalyst filter 106 face relative to the sides of the cabin enclosure. These terms are not intended to limit the scope of this disclosure. In some embodiments, for example, the lamp 108 may be mounted proximal to the bottom side b of the cabin enclosure 102. It will be understood that the orientation of the catalyst filter 106 can be re-oriented to accommodate re-positioning of the of the lamp 108 so that the catalyst-coated surfaces 116*a-c* substantially face the lamp 108 positioned proximal to the bottom side b of the cabin enclosure 102.

Cabin Enclosure 102

Referring to FIGS. 3, 4, 5, 6, and 10, the cabin enclosure 102 may comprise generally a rectangular enclosure shape having a top wall 122 (also referred to as side a), a back wall 124, and a bottom wall 126 (also referred to as side b). A parts access opening 132 in the cabin enclosure 102 may be configured to receive the filter 104, the catalyst filter 106, the lamp 108, the reflector 110 and at least portions of the control assembly 112 into the cabin enclosure 102. When the filter system 100 is fully assembled, as shown in FIGS. 4 and 5, the cabin enclosure 102 may be configured to receive unfiltered air in an inlet opening on the back side c and allow filtered air to pass out of an outlet opening located on the front side d of the rectangular enclosure shape.

The cabin enclosure 102 may constructed from one or more pieces of sheet metal fastened to form the enclosure shape, described above. The structure of the sheet metal pieces may be reinforced with ridges (e.g. first ridge 158*a*) extending along the surfaces of the top, bottom, and back walls of the cabin enclosure 102. The one or more pieces of sheet metal may be fastened together clinching the sheet metal pieces using TOX® (a trademark of PRESSOTECHNIK GmbH & Co. KG) joints. It will be understood by persons of ordinary skill in the art that the cabin enclosure 102 may be subject to variations, modifications, changes, and substitutions, including but not limited to changes in size, number of parts, operations, profile of form features, and placement of parts. The cabin enclosure may employ other types of fasteners, including but not limited to screws, clips, bolts, rivets, and adhesives.

Catalyst Filter 106

Figure 15:
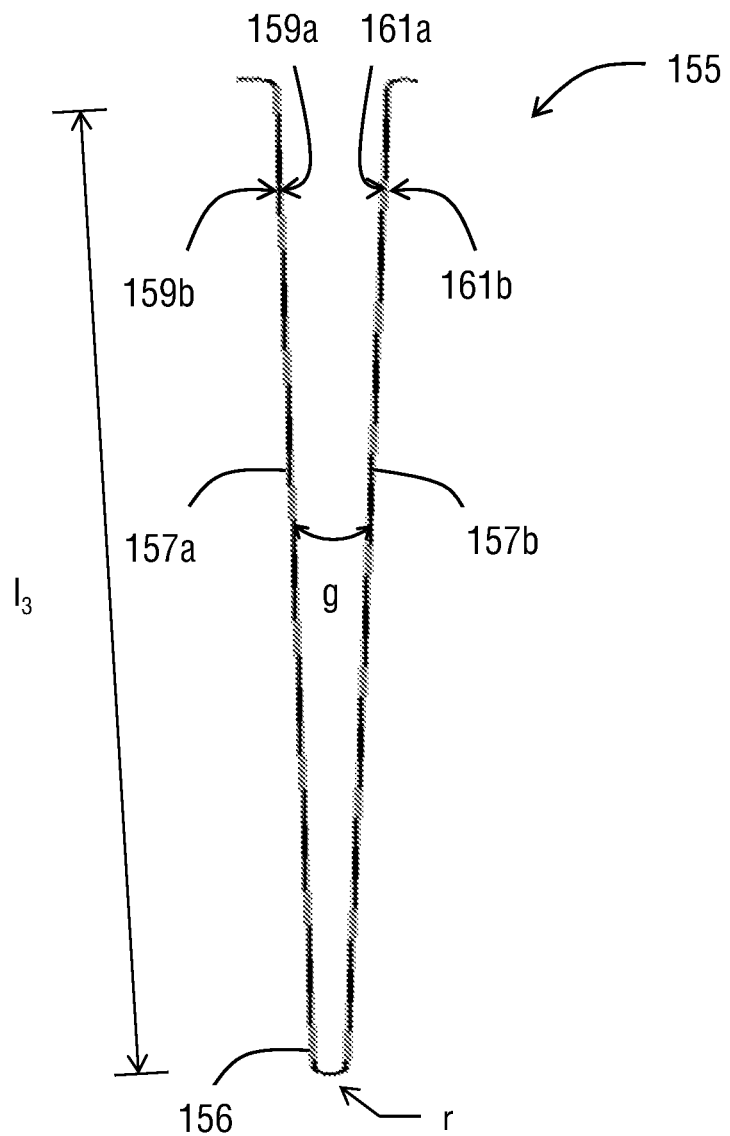
FIG. 15 is an illustration of a wave segment of a catalyst filter.

Referring to FIGS. 7, 9, and 15, the catalyst filter 106 may comprise a filter shape. The filter may comprise one or more segments 155. Each segment 155 may comprise a first band 157a comprising and a second band 157b. Each band 157a, 157b may comprise a first length $l_3$ of substantially flat material extending longitudinally along the length $l_3$. Each band 157a, 157b may comprise a first wall 159a, 161a and a second wall 159b, 161b, respectively. Each first wall 159a, 161a faces an opposite direction from the respective second wall 159b, 161b. Each respective first wall 159a, 161a or second wall 159b, 161b may be coated with a catalyst material, or both.

The first band 157a and second band 157b may diverge relative to each other across the length $l_3$. In some embodiments, the first walls of each band of the catalyst filter 106 (e.g. first wall 159a, 161a) may be optically exposed to light from at least the lamp 108. For example, in FIG. 10 the lamp 108 may emit light between respective bands of each segment for reception of light on the catalyst-coated surfaces 116a, 116b of the each band. The catalyst-coated surfaces 116a, 116b may be optically exposed to the light from the lamp 108 without being at least partially blocked by one of the bands of the catalyst filter 106 or other structure of the catalyst filter 106.

The first band 157a and second band 157b may extend continuously along its longitudinal length $l_3$, substantially traversing the length of the catalyst filter 106 without being intersected by other structure of the catalyst filter 106. In some embodiments, the segment 155 may comprise a connecting portion 156 connecting the first band with the second band and with each first and second band 157a and 157b extending from each of two ends of the connecting portion 156.

In some embodiments, the connecting portion 156 comprises a rounded shape having an arc with a radius r. Each band 157a and 157b may extend from a respective end of the arc portion at an angle g between the two bands 157a and 157b.

In other embodiments, the connecting portion 156 may be comprise a sharp bend, e.g. a v-shape, a square or multi-cornered shape with the bands 157a, 157b extending from ends of the connecting portion 156 to form a segment of the filter shape. In other embodiments, the first band 157a and second band 157b may be housed in the cabin enclosure with no connecting portion 156 connecting the first band 157a and second band 157b.

Referring to FIG. 9, one or more segments 155a, 155b may comprise a continuous wavy pattern, as shown in FIG. 9. For convenience, only two of the segments (e.g. 155a and 155b) have been provided reference numerals. It will be understood that additional substantially similar segments may be extend in series to the desired length $l_w$.

The wavy pattern may comprise one or more segments (e.g. 155a and 155b) forming the filter shape, including but not limited to a sinusoidal shape, a zig-zag shape, a square wave shape, a W-shape, a U-shape, and a V-shape, among other configurations readily apparent to those skilled in the art. In some embodiments, each segment of the wavy pattern may comprise a different size or shape, and the connecting portions 156 may comprise different shapes from one segment to another. In other embodiments, the bands of each segment may comprise a non-flat surface, including but not limited to corrugated surfaces, among other non-planar configurations known in the art.

The base structure 140 may comprise one or more bands of metal configured to bend or be formed into a filter shape, described above. In some embodiments, as shown in FIGS. 7, 8, 9, and 10, the base structure 140 may comprise an aluminum foil band having a width $t_3$ that is bent by known means into a series of wave segments to extend to a length $l_w$ to form structure shape. The width $t_3$ of the band may be varied to vary the surface area of the catalyst-coated and carbon coated surfaces.

The base structure 140 may comprise a height h, which is generally the height of each wave segment (e.g. wave segment 155a and 155b). The catalyst and carbon coatings applied to the base structure may provide rigidity to maintain the shape of the base structure 140 and prevent warping.

In one embodiment of the catalyst filter 106, the length $l_w$ may comprise 25 inches (in.); the height h may comprise 19.2 in., the width $t_3$ may comprise 1.2 in.; the radius of the arc of the rounded connecting portion 156 may comprise about 0.15 in.; and the separation angle g between the two bands of each wave segment comprises about two (2) degrees. It will be understood that the dimensions of the catalyst filter 106 may be varied to accommodate the design of the filter system 100, including but not limited to the desired size of the cabin enclosure 102.

Given the dimensions above in Paragraph [0030], the total surface area of the catalyst filter 106 may comprise about $1.886e+02$ in.$^2$. The catalyst-coated surfaces and absorbent material-coated surfaces extending along the base structure 140 comprise about forty percent (40%) catalyst-coated surfaces and about sixty percent (60%) absorbent material-coated surfaces of the total surface area of the catalyst filter 106. It will be understood by persons of ordinary skill that total surface area of the catalyst filter 106 and the percentage of catalyst-coated surfaces and carbon coated surfaces extending along the base structure 140 may be varied to meet filtering and purification requirements.

Referring to FIG. 3, the catalyst filter 106 may be set within an insert frame 136. Frame members 138 of the insert frame 136 comprise bars extending around from the top to the bottom and across the front and back of the catalyst filter 106. The insert frame 136 may prevent bending and twisting of the catalyst filter 106, when the catalyst filter 106 is set within the cabin enclosure 102. The frame members 138 extending across the front and back of the catalyst filter 106 may comprise a thickness and cover a surface area of the front and back of the catalyst filter 106 to allow for air to freely flow through the structure of the frame without a substantial drop in air pressure due to any blockage by the insert frame 136. The insert frame 136 may be secured to the catalyst filter 106 with a button feature 139, as shown in FIG. 6.

Lamp 108

Figure 12:
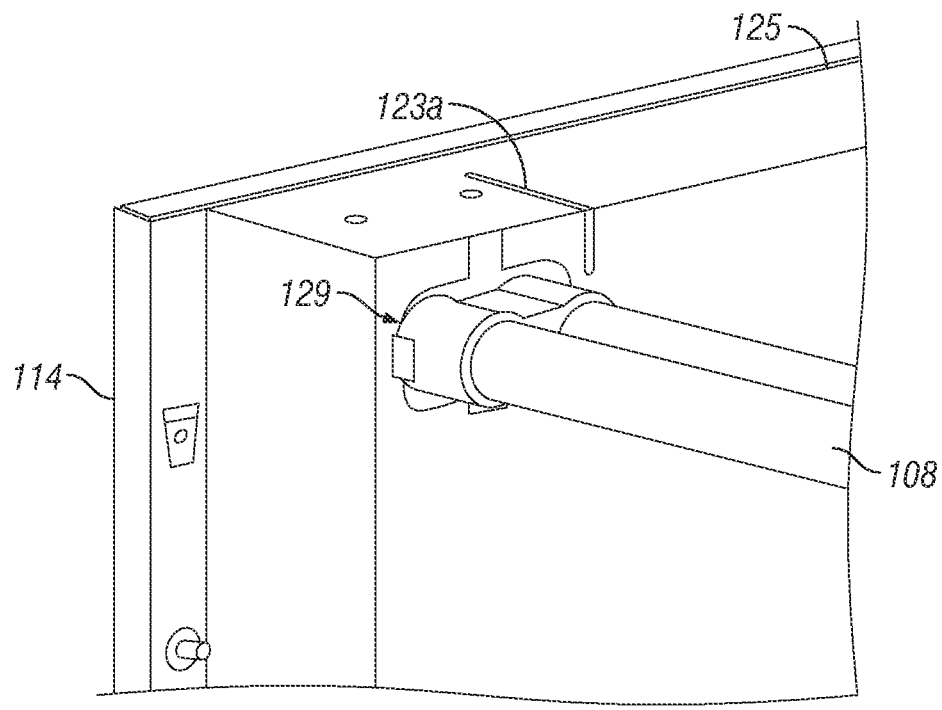
FIG. 12 is a view of a lamp in a socket of a control assembly.

Referring to FIG. 12, the lamp 108 may operationally couple to a control assembly 112. For example, the lamp 108 may plug into an electric first socket 129 in the control assembly 112. The lamp 108 may comprise a light bulb having a wattage configured to create a sufficient reaction between the catalyst material and the light generated by the bulb for the purification of air. In some embodiments, the wattage of the lamp 108 may comprise about 55 watts (W). It will be understood by persons or ordinary skill in the art that the wattage of the bulb of the lamp 108 may be varied to increase or decrease the reaction between the catalyst material and the light generated by the bulb for the purification of air.

In some embodiments, as shown in FIG. 7, the lamp 108 has a length $l_1$ configured to extend from where the lamp 108 couples to the first socket 129 outward over the top of the catalyst filter 106. The length $l_1$ may be configured to illuminate the catalyst-coated surfaces of each of the top-facing corridors along the length $l_w$ of the catalyst filter 106, including top-facing corridors 118a, b, shown in FIG. 10. In some embodiments, the length $l_1$ is not as long as the length $l_w$. For example, $l_w$ may be about 25 in. and $l_1$ may be about 21 in.

Reflector Frame 110

Figure 13:
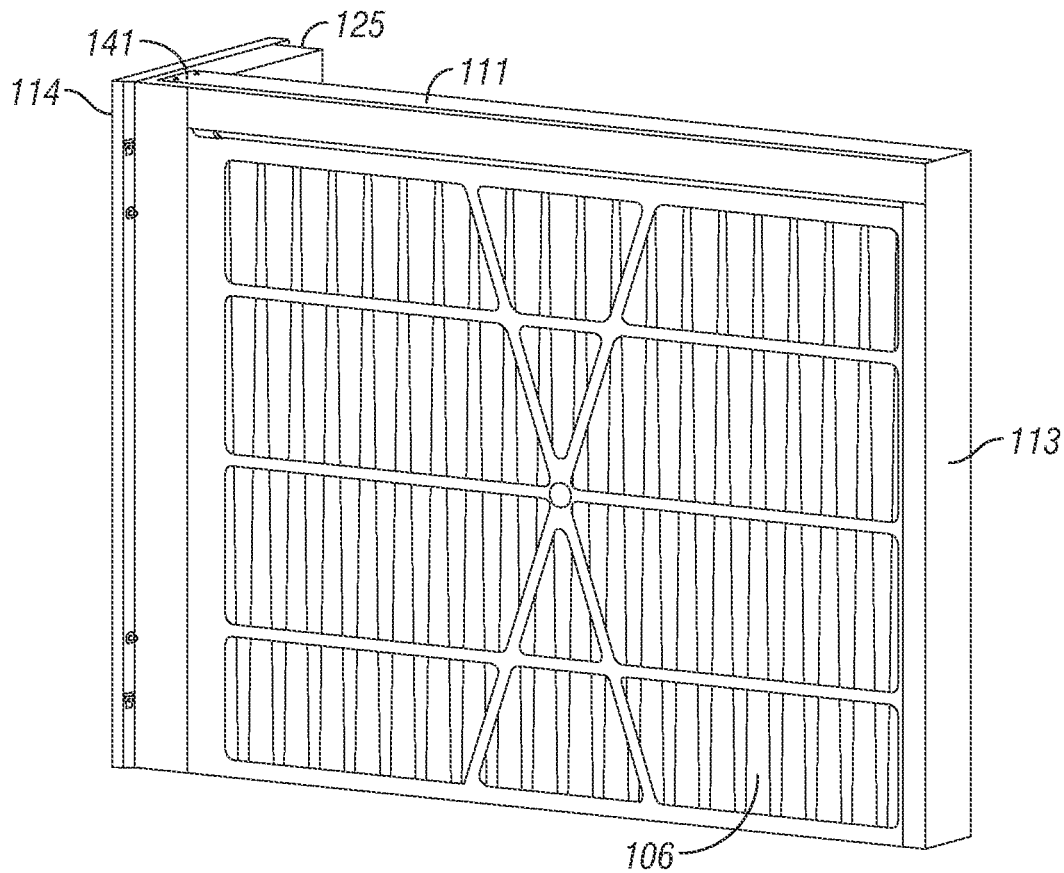
FIG. 13 is a view of an assembly comprising a control assembly, door, reflector frame, and a first catalyst filter.

Referring to FIGS. 3, 12, and 13, the reflector frame 110 may couple to the control assembly 112 at or near the top and at or near the bottom of the control assembly 112. The reflector frame 110 may comprise the top arm 111 extending from a top portion of the control assembly 112. The reflector frame 110 may further comprise a back arm 113 and a bottom arm 115 that together with the top arm 111 form substantially a rectangular u-shape. An open end of the u-shape may be configured to receive the insert frame 136 with the catalyst filter 106 set within it.

The top arm 111 may be configured to extend over the top and the front and back sides of the lamp 108, when a free end of the top arm 111 is coupled at or near the top of the control assembly 112. The back arm 113 and the bottom arm 115 may extend around the back and bottom portion of the insert frame 136. The reflector frame 110 may support and maintain the insert frame 136 with the catalyst filter 106 within the cabin enclosure 102 and prevent twisting, bending, and other misalignment of the catalyst filter 106.

The top arm 111 of the reflector frame 110 may extend on top of the lamp 108 and over the catalyst filter 106. As shown in FIG. 5, the reflector frame 110 may be configured to comprise the reflective surface 142 contained within a portion of a wall of the top arm 111 facing the top portion of the catalyst filter 106 to reflect UV light from the lamp 108 onto the catalyst-coated surfaces (e.g. catalyst-coated surfaces 116a-c, shown in FIG. 10) of the catalyst filter 106.

The reflective surface 142 may comprise a single side of a polished aluminum sheet. In other embodiments, other materials may be used as a reflective surface including but not limited to use of a polished portion of the undersurface of the top arm 111 without using separate reflector to obtain the desired reflective surface, or using a reflective sheet that is adhered to the upper arm of the reflector frame 110.

Referring FIGS. 3, 12, and 13, an end portion 141 of the top arm 111 may slide into a first slot 123a within the control enclosure 125. An end portion of the bottom arm 115 may slide into a second slot 123b within control enclosure 125. The top arm 111 and the bottom arm 115 may be secured to the control enclosure 125 at each respective, first slot 123a and second slot 123b by a rivet joint or other suitable fastener.

Control Assembly 112 and Door 114

Referring to FIGS. 3, 6, and 12, the control assembly 112 may comprise a control enclosure 125 housing components for operation of the lamp 108, including a ballast, surge protector, and a switch (not shown). It will be understood by persons of ordinary skill in the art that other components necessary for the operation of the filter system 100 may be included in the control assembly, including but not limited to electrical leads to an external electrical control system (not shown).

A cabin door 114 may couple to one side of the control assembly 112. The cabin door 114 may be configured to cover the parts access opening 132 (shown in FIG. 3) and lock into the cabin enclosure 102 to secure the filter system 100 as one unit. The cabin door 114 may comprise a handle 144 or other manual control devices for removal of the cabin door 114 and to allow users to access the parts of the filter system 100 contained in the cabin enclosure 102.

The cabin door 114 may further comprise a power connector 146 configured to operationally couple to electrical leads to power one or more lamps, such the lamp 108. The power connector 146 may comprise an electrical socket extending through or accessible through an opening 147 in the surface of the cabin door 114.

The cabin door 114 may further comprise a first eye hole 148 configured to allow a user to verify that one or more lamps, such as the lamp 108, contained in the cabin enclosure 102 are operating. The first eye hole 148 may comprise a circular opening in the surface of the cabin door 114. The opening may be sealed with a transparent glass or plastic lens to prevent contaminants from escaping through the eye hole 148. The first eye hole 148 may operate in conjunction with a second eye hole 149. The second eye hole 149 may extend through a wall of the control enclosure 125. The first eye hole 148 and second eye hole 149 may be substantially aligned to allow a user to look through the first eye hole 148 and through the second eye hole 149 to determine whether the lamp 108 is turned on.

Assembly of the First Filter System 100

Referring to FIGS. 3 and 6, the filter 104 may be inserted into the cabin enclosure 102 through the front opening 132 and slid along filter rails 134a, b until the filter 104 reaches the back wall 124. The reflector frame 110 having the catalyst filter 106 contained within the reflector frame 110 and the control assembly 112 and door 114 attached to the reflector frame may be slid into the cabin enclosure 102. The reflector frame 110 may slide along reflector frame rails 135a, b until the reflector frame 110 reaches the back wall 124.

One or more snap fasteners 127a and 127b shown in FIG. 6 may fasten the cabin door 114 and control enclosure 125 together. Snap fasteners 127a and 127b may comprise strike and lock fasteners manufactured by ITW Fastex®. It will be understood by persons of ordinary skill in the art that other fasteners may replace the one or more snap fasteners 127a, 127b, shown in FIG. 6, or the panel fasteners, including but not limited to screws, snap or interference fits, hooks, and latches.

Second Filter System 200

Figure 11:
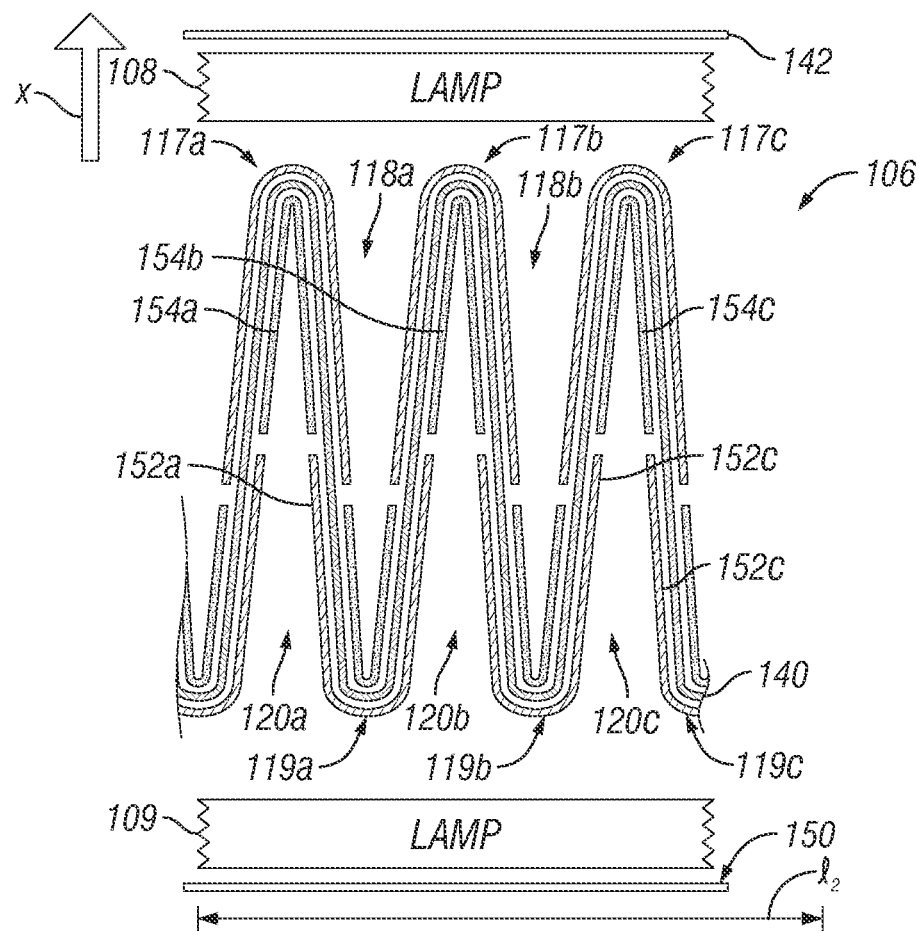
FIG. 11 is an illustration of coating on a second catalyst filter.
Figure 14:
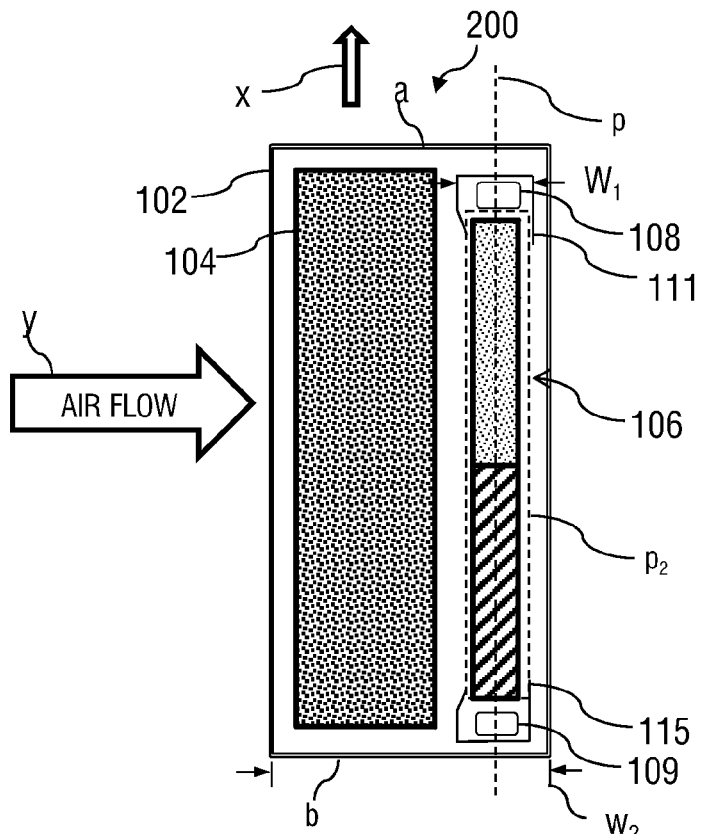
FIG. 14 is a cross section facing the side of a second filter system.

In a second embodiment of a filter system, a second filter system 200, as shown in FIGS. 11, and 14, may comprise a second lamp 109 may be mounted proximal to the bottom of the cabin enclosure 102 within the enclosure 102 so that one or more of the catalyst-coated surfaces 152a-c of the bottom-facing corridors 120a-c receive UV light for the purification of air. At least a portion of the second lamp 109 may be positioned within the first plane p to emit light substantially in the first direction into one or more of the bottom-facing corridors 120a-c. The second lamp 109 may plug into a second socket (not shown) in the control assembly 112 and may be operationally connected to the components of the control assembly 112, including the power connection 146.

Referring to FIG. 11, the wavy pattern structure of the catalyst filter 106 may comprise the catalyst-coated surfaces 152a-c for air purification. A coating of each catalyst-coated surface 152a-c may be applied over the underlying base structure 140. The catalyst-coated surfaces 152a-c may extend along the bottom-facing corridors 120a-c and be configured to receive light from the second lamp 109.

Referring to FIG. 11, the wavy pattern structure may further comprise carbon-coated surfaces 154a-c, which are coated with a carbon-based material for absorbing contaminants. The carbon-coated surfaces 154a-c may comprise one or more carbon-coated surfaces extending along at a portion of the walls of each bottom-facing corridor 118*a-c*, including over the troughs 119*a-c*. Each bottom-facing corridor 118*a-c* may comprise at least one catalyst-coated surface 152*a-c* and at least one carbon-coated surface 154*a-c*.

Referring to FIG. 14, the bottom arm 115 of the reflector frame 110 may extend under the second lamp 109 and beneath the catalyst filter 106, in a manner similar to the top arm 111 extending over the first lamp 108, as shown in FIG. 5. The reflector frame 110 may be configured to comprise a reflective surface 150 (shown in FIG. 11) contained within a portion of a wall of the bottom arm 115 facing the bottom portion of the catalyst filter 106 to reflect UV light from the second lamp 109 onto the catalyst-coated surfaces of the catalyst filter 106.

The reflective surface 150 may comprise a single side of a polished aluminum sheet. In other embodiments, other materials may be used as a reflective surface including but not limited to use of a polished portion of the undersurface of the bottom arm without using separate reflector to obtain the desired reflective surface, or using a reflective sheet that is adhered to the bottom arm 115.

The second lamp 109 may comprise a UV bulb having a wattage configured operate in conjunction with the wattage of the first lamp 108 to create a sufficient reaction between the catalyst material and the light generated by the bulb for the purification of air. In some embodiments, the wattage of the first lamp 108 may comprise about 55 W and the wattage of the second lamp 109 may comprise about 55 W. It will be understood by persons or ordinary skill in the art that the wattage of the bulb of the first lamp 108 and the second lamp 109 may be varied to increase or decrease the catalyst reaction. In some embodiments, the second lamp 109 has a length $l_2$ to extend from one end of the top of the catalyst filter 106 to the other.

Referring to FIGS. 7, 8, 11, and 14, the dimensions of the catalyst filter 106 may be configured to accommodate the second lamp 109 positioned under the catalyst filter 106 and to prevent the heightening the cabin enclosure 102. For example, the height h of the catalyst filter 106 (shown in FIG. 8) may comprise about 17.7 in. The catalyst-coated surfaces and absorbent material-coated surfaces extending along the base structure may comprise about 50% catalyst-coated surfaces of the total surface area and about 50% carbon-coated surfaces of the total surface area. The remaining dimensions of the catalyst filter 106 may remain the same as cited for a single-lamp configuration in Paragraph [0030].

The height h of the catalyst filter 106 modified to accommodate the second lamp 109 may reduce the total surface area of the catalyst filter 106 to about 1.7405e+03 in.² which is a reduction in surface area available for catalyst coating compared to the total surface area (cited as an example) for the catalyst filter 106 in the single lamp configuration. The effect of the reduction in surface area may offset by the addition of catalyst-coated surfaces 152*a-c* on the bottom-facing corridors 120*a-c* of the catalyst filter 106, shown in FIG. 11.

Third Filter Assembly 300

Figure 16:
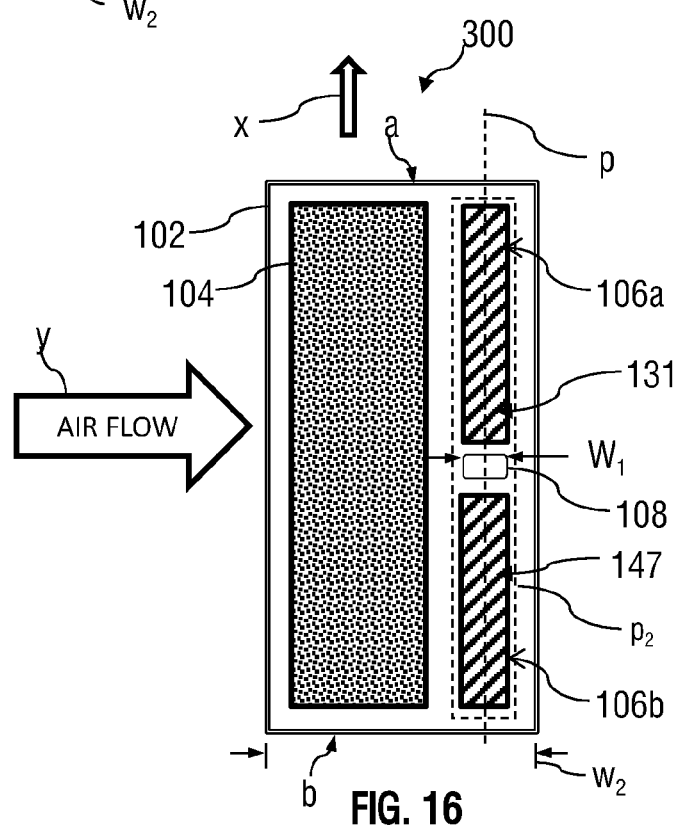
FIG. 16 is a cross section facing the side of a third filter system.

Alternatively, as shown in FIG. 16, the insert 106 of the filter system 100 may be utilized in a third filter system 300. In this embodiment, the insert 106 may comprise a first filter part 106*a* and a second filter part 106*b*. Each of the first part 106*a* and the second part 106*b* may comprise a wavy pattern in the manner shown for the insert 106 shown in FIGS. 7, 8, and 9, except that the dimensions may be adjusted to accommodate two parts aligned from the top side a to the bottom side b of the enclosure 102 within the first plane p.

The first filter part 106*a* and the second filter part 106*b* may be mounted within the cabin enclosure 102. The lamp 108 may be positioned between in spacing area s1 the two filter parts 106*a* and 106*b*. The cabin enclosure 102 of the first filter system 100 may be modified to accommodate repositioning of the lamp 108.

Figure 17:
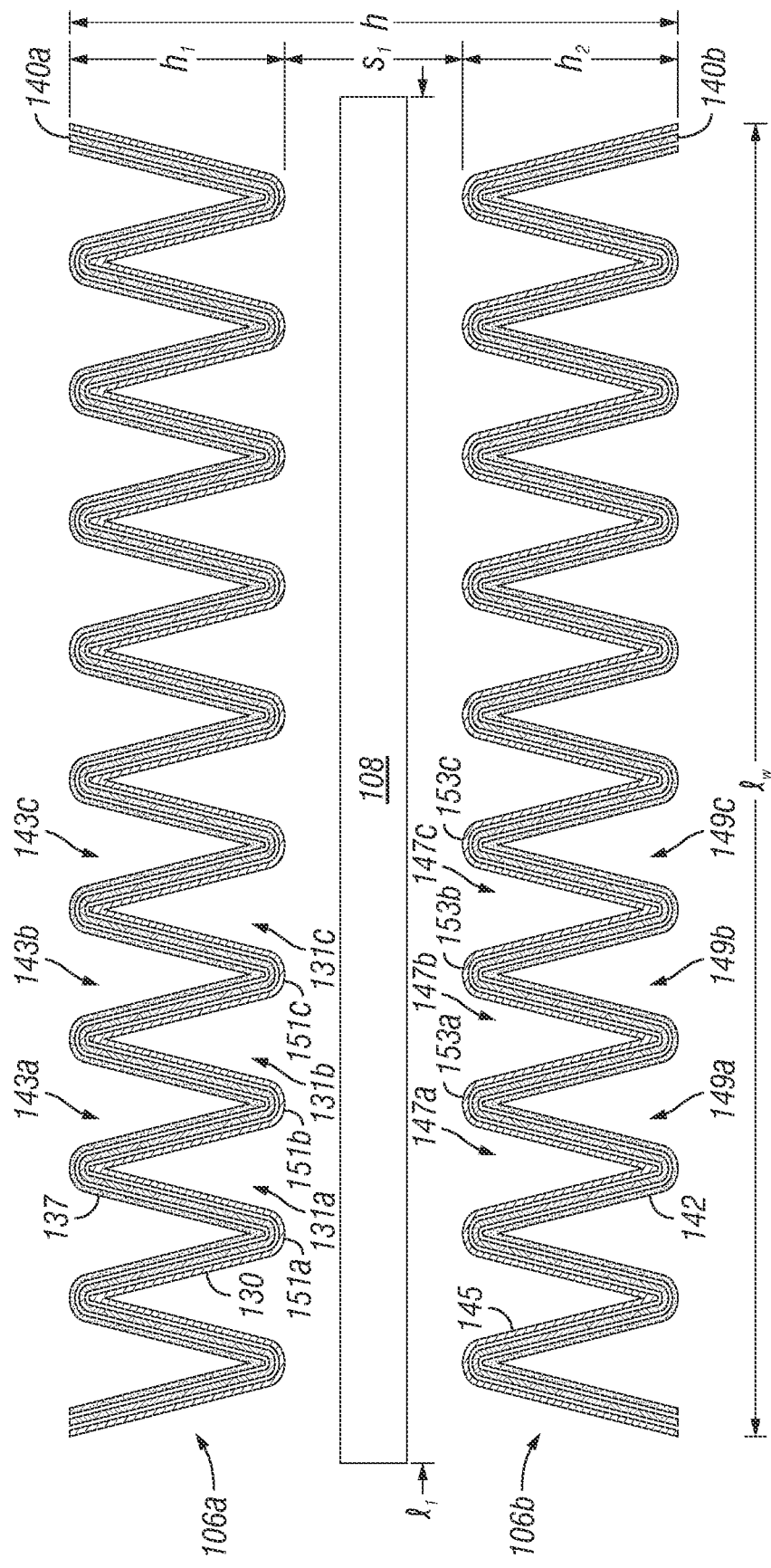
FIG. 17 is an illustration of coating on a third catalyst filter.

Referring FIG. 17, each filter part 106*a*, 106*b* may comprise a coating along the base structure 140 of the wavy pattern. First filter part 106*a* may comprise catalyst-coated surfaces 130 extending along first lamp-facing corridors 131*a-c* (shown as first lamp-facing corridor 131 in FIG. 16). Carbon-coated surfaces 137 may extend along corridors 143*a-c* on an opposite side of the base structure 140*a* from the first lamp-facing corridors 131*a-c*.

Second filter part 106*b* may comprise catalyst-coated surfaces 145 extending along second lamp-facing corridors 147*a-c* (shown as second lamp-facing corridor 147 in FIG. 16). Carbon-coated surfaces 142 may extend along corridors 149*a-c* on an opposite side of the base structure from the second lamp-facing corridors 147*a-c*.

Referring to FIGS. 16 and 17, at least a portion of the lamp 108 may be positioned aligned within the first plane p or at least partially within a perimeter $p_2$ of the catalyst filter 105 to emit light substantially in the first direction x into one or more of the first lamp-facing corridors 131*a-c* of the filter part 106*a* or one or more of the second lamp-facing corridors 147*a-c* of the second filter part 106*b* or into both. At least a portion of the catalyst-coated surfaces 130, 145 of each of the first filter part 106*a* and second filter part 106*b* may substantially face the lamp 108 to receive direct UV light from the lamp 108. For example, the surfaces of troughs 151*a-c* of the first filter part 106*a* and crests 153*a-c* of the second filter part 106*b* may substantially face the lamp 108 to receive direct light. The first lamp-facing corridors 131 may also substantially face the bottom side b, and the second lamp-facing corridors 147 may also substantially face the top side a, as shown in the configuration in FIG. 16.

The height $h_1$ of the first filter part 106*a*, spacing $s_1$, and the height $h_2$ of the second filter part 106*b* may be configured to total the substantially the same height h of the insert 106, shown in FIG. 7 for the one-lamp configuration. The first filter part 106*a* and the second filter part 106*b* may be substantially identical in dimensions and in the coating pattern over the base structure 140*a* and 140*b*, respectively. One of the first filter part 106*a* or second filter part 106*b* may be flipped relative to the other to allow light from the lamp 108 to emit into the respective lamp-facing corridors 131*a-c* and 147*a-c* having catalyst-coated surfaces 130, 145, respectively.

Cabin Width $w_2$

Referring to FIGS. 5, 14, and 16, the cabin enclosure 102 shown in the first filter system 100, the second filter system 200 and the third filter system 300 may comprise a cabin width $w_2$. In some embodiments, the cabin width $w_2$ may include a reflector width $w_1$, which is equal to the width of the top arm 111 of the reflector frame 110 taken generally along the same direction as the cabin width $w_2$. The reflector width $w_1$ includes the width of the lamp 108. In the third filter system, the width $w_1$ comprises the width solely of the lamp 108. In the embodiments shown, aligning the top arm 111 (shown in FIGS. 5 and 14) or the lamp 108 or both in the direction x with the catalyst filter 106 within the plane p may save space within the cabin enclosure 102 and allows the cabin width $w_2$ to be reduced.

In some embodiments, the cabin width $w_2$ may comprise about 8.5 in. The same advantage in cabin width $w_2$ reduction may be realized when the second lamp 109 along with the bottom arm 115 are utilized, as shown in FIG. 14, because the position of the second lamp 109 and bottom arm 115 below and in alignment with the catalyst filter 106 within the plane p does not widen the cabin enclosure about the cabin width $w_2$.

Position of the Lamps 108, 109

Referring to FIGS. 14 and 18, one or more of the lamps 108, 109 may be disposed substantially outside of the flow of air through the catalyst filter 106. The lamps 108, 109 may be disposed within the housing at a location that does not substantially reduce the flow of air through the cabin enclosure 102 to the catalyst filter 106.

Referring to FIG. 18, the catalyst filter 106 may comprise the perimeter $p_2$. The perimeter $p_2$ may comprise a perimeter height dimension $h_3$ and a perimeter width dimension $w_3$, shown in FIG. 18. The perimeter height dimension $h_3$ may traverse the catalyst filter 106 at any location along the perimeter width dimension $w_3$ so that the perimeter height dimension $h_3$ is constant. The perimeter width dimension $w_3$ may traverse the catalyst filter 106 at any location along the perimeter height dimension $h_3$ so that the perimeter width dimension $w_3$ is constant.

The perimeter $p_2$ may be coincident, intersecting or aligned with the plane p of the catalyst filter 106. One or both of the lamps 108, 109 may be disposed adjacent to the catalyst filter 106, intersecting or aligned with the plane p of the catalyst filter 106, and outside the flow of air into the catalyst filter 106.

A first height plane $p_3$ may be aligned with the flow of air through the housing 102 (for clarity the enclosure 102 is not shown in FIG. 18) and extend through the catalyst filter perimeter $p_2$ to define a start of the perimeter height dimension $h_3$. A second height plane $p_4$ may be aligned with the flow of air in the direction y through the enclosure 102 and extend through the catalyst filter perimeter $p_2$ to define an end of the perimeter height dimension $h_3$. A first width plane $p_5$ may be aligned with the flow of air through the enclosure 102 and extend through the catalyst filter perimeter $p_2$ to define a start of the perimeter width dimension $w_3$. A second width plan $p_6$ may be aligned with the flow of air through the enclosure 102 and extend through the catalyst filter perimeter $p_2$ to define an end of the perimeter width dimension $w_3$ In some embodiments, no portion of the first lamp 108 may be positioned on the side of the second height plane $p_4$ or side of the second width plane $p_6$ where the catalyst filter 106 is disposed. The first lamp 108 may be disposed outside of the volume defined by the first height plane $p_3$, the second height plane $p_4$, the first width plane $p_5$, and the second width plan $p_6$, which as shown contains the catalyst filter 106.

In some embodiments, positioning one or more lamps 108, 109 above and/or below and in alignment with the catalyst filter 106, i.e. in the first plane p and/or outside the flow of air in the direction y through the enclosure 102, has the advantage of removing the lamps and reflector surfaces from the path of air flow in the direction y. The air flow is not disrupted by the lamps and reflector surfaces, allowing the filter system to operate with greater efficiency.

Having thus described the present invention by reference to certain of its preferred embodiments, it is noted that the embodiments disclosed are illustrative rather than limiting in nature and that a wide range of variations, modifications, changes, and substitutions are contemplated in the foregoing disclosure and, in some instances, some features of the present invention may be employed without a corresponding use of the other features. Many such variations and modifications may be considered desirable by those skilled in the art based upon a review of the foregoing description of preferred embodiments. Accordingly, it is appropriate that the appended claims be construed broadly and in a manner consistent with the scope of the invention.

The invention claimed is:

1. A filter system for purifying air comprising:
a first light source;
a second light source;
a catalyst filter configured for placement in a filter housing;
wherein the catalyst filter comprises a first band and a second band of material;
the first band and second band of material each respectively comprising:
a first length of longitudinally extending material; and
a first wall and a second wall formed by the material, the first and second walls facing opposite directions;
wherein at least a portion of the first wall of each of the first and second bands of material is coated with a catalyst material;
wherein the catalyst material of the first and second bands, upon receiving light emitted by a light source disposed to emit light onto the catalyst material, is capable of breaking down contaminants in the air passing through the housing and over the catalyst material;
wherein the first and second bands of material each extend continuously along its longitudinal axis, substantially traversing the catalyst filter without being intersected by other structure of the catalyst filter;
wherein the first and second bands of material diverge relative to each other across the catalyst filter and wherein the first walls of the respective first and second bands of material are optically exposed to each other, such light from a light source at least partially disposed to emit light between the first and second bands of material is received on the catalyst material of the first walls of both the first and second bands of material without being at least partially blocked by one of the first and second bands or other structure of the catalyst filter;
wherein the first light source is at least partially disposed to emit light between the first and second bands of material and shining light on the catalyst material of the first walls of both the first and second bands of material without being at least partially blocked by one of the first and second bands or other structure of the catalyst filter;
wherein at least a portion of the first wall of each of the first and second bands of material is coated with an absorbent material configured to absorb one or more by-products produced by the reaction of catalyst material with contaminants in the air;
wherein the second light source is at least partially disposed to emit light on the catalyst material of the second walls of both the first and second bands of material without being at least partially blocked by one of the first and second bands or other structure of the catalyst filter;
wherein at least a portion of the second wall of each of the first and second bands of material is coated with a catalyst material;
wherein at least a portion of the second wall of each of the first and second bands of material is coated with an absorbent material configured to absorb one or more by-products produced by the reaction of catalyst material with contaminants in the air; and
wherein the catalyst filter comprises an aluminum base structure having catalyst-coated surfaces and absorbent material-coated surfaces extending along the surfaces the first wall and the second wall of the first band and the second band, respectively, and wherein the catalyst filter comprises the following:

the width of the first band and the second band each comprise about 1.2 inches (in.);
a rounded portion connecting the first band and the second band, the rounded portion comprising an arc portion having a radius of about 0.15 in.;
the first band diverges from the second band at an angle of about 2 degrees;
a height of the catalyst filter comprises about 17.7 in.;
the length of the catalyst filter comprises about 25 in.; and
fifty percent (50%) of the total surface area of the first wall and the second wall of the first band and the second band, respectively, comprises catalyst-coated surfaces, and fifty percent (50%) of the total surface area of the first wall and the second wall of the first band and the second band, respectively, comprises absorbent material-coated surfaces.

2. The filter system of claim 1,
wherein the first light source is disposed substantially outside the flow of air to the catalyst filter.

3. The filter system of claim 1,
wherein the first light source is disposed within the housing at a location that does not substantially reduce the flow of air through the housing to the catalyst filter.

4. The filter system of claim 1,
wherein the catalyst filter has a perimeter and the first light source is disposed adjacent to the perimeter of the catalyst filter and outside the flow of air to the catalyst filter.

5. The filter system of claim 1,
wherein the catalyst filter has a perimeter with dimensions of a perimeter height and a corresponding perimeter width, which dimensions define a filter plane; and
wherein the first light source is disposed adjacent to the catalyst filter, intersecting or aligned with the filter plane, and outside the flow of air into the catalyst filter.

6. The filter system of claim 1,
wherein the catalyst material comprises titanium dioxide, and the absorbent material comprises carbon.

7. The filter system of claim 6,
wherein the first band and second band extend from a first end and a second end of the rounded portion, respectively; and wherein the first band, the rounded portion, and the second band form a continuous wavy pattern along the a length of the catalyst filter.

8. The filter system of claim 7,
wherein the catalyst filter comprises an aluminium base structure having catalyst-coated surfaces and absorbent material-coated surfaces extending along the surfaces the first wall and the second wall of the first and second band, respectively, and wherein the catalyst filter further comprises the following:
the width of the first band and the second band each comprise about 1.2 inches (in.);
the rounded portion comprises an arc portion having a radius of about 0.15 in.;
the first band diverges from the second band at an angle of about 2 degrees;
a height of the catalyst filter comprises about 19.2 in.;
the length of the catalyst filter comprises about 25 in.; and
forty percent (40%) of the total surface area of the first wall and the second wall of the first band and the second band, respectively, comprises catalyst-coated surfaces, and sixty percent (60%) of the total surface area of the first wall and the second wall of the first band and the second band, respectively, comprises absorbent material-coated surfaces.

9. The filter system of claim 1,
wherein the second light source is disposed substantially outside the flow of air to the catalyst filter.

10. A filter system for purifying air comprising:
a first light source;
a catalyst filter configured for placement in a filter housing;
wherein the catalyst filter comprises a first band and a second band of material;
the first band and second band of material each respectively comprising:
a first length of longitudinally extending material; and
a first wall and a second wall formed by the material, the first and second walls facing opposite directions;
wherein at least a portion of the first wall of each of the first and second bands of material is coated with a catalyst material;
wherein the catalyst material of the first and second bands, upon receiving light emitted by a light source disposed to emit light onto the catalyst material, is capable of breaking down contaminants in the air passing through the housing and over the catalyst material;
wherein the first and second bands of material each extend continuously along its longitudinal axis, substantially traversing the catalyst filter without being intersected by other structure of the catalyst filter;
wherein the first and second bands of material diverge relative to each other across the catalyst filter and wherein the first walls of the respective first and second bands of material are optically exposed to each other, such light from a light source at least partially disposed to emit light between the first and second bands of material is received on the catalyst material of the first walls of both the first and second bands of material without being at least partially blocked by one of the first and second bands or other structure of the catalyst filter;
wherein the first light source is at least partially disposed to emit light between the first and second bands of material and shining light on the catalyst material of the first walls of both the first and second bands of material without being at least partially blocked by one of the first and second bands or other structure of the catalyst filter;
wherein at least a portion of the first wall of each of the first and second bands of material is coated with an absorbent material configured to absorb one or more by-products produced by the reaction of catalyst material with contaminants in the air;
wherein at least a portion of the second wall of each of the first and second bands of material is coated with an absorbent material configured to absorb one or more by-products produced by the reaction of catalyst material with contaminants in the air;
wherein the catalyst material comprises titanium dioxide, and the absorbent material comprises carbon;
wherein the catalyst filter comprises a rounded portion connecting the first band and the second band;
wherein the first band and second band extend from a first end and a second end of the rounded portion, respectively; and wherein the first band, the rounded portion, and the second band form a continuous wavy pattern along the a length of the catalyst filter; and
wherein the catalyst filter comprises an aluminum base structure having catalyst-coated surfaces and absorbent material-coated surfaces extending along the surfaces the first wall and the second wall of the first and second band, respectively, and wherein the catalyst filter further comprises the following:

the width of the first band and the second band each comprise about 1.2 inches (in.);

the rounded portion comprises an arc portion having a radius of about 0.15 in.;

the first band diverges from the second band at an angle of about 2 degrees;

a height of the catalyst filter comprises about 19.2 in.;

the length of the catalyst filter comprises about 25 in.; and forty percent (40%) of the total surface area of the first wall and the second wall of the first band and the second band, respectively, comprises catalyst-coated surfaces, and sixty percent (60%) of the total surface area of the first wall and the second wall of the first band and the second band, respectively, comprises absorbent material-coated surfaces.

* * * * *